United States Patent [19]

Uematsu et al.

[11] Patent Number: 5,948,615
[45] Date of Patent: Sep. 7, 1999

[54] METHOD FOR ANALYSIS OF NUCLEIC ACID AND DNA PRIMER SETS FOR USE THEREIN

[75] Inventors: Chihiro Uematsu, Kokubunji; Hideki Kambara, Hachioji, both of Japan

[73] Assignee: Hitachi, Ltd., Tokyo, Japan

[21] Appl. No.: 08/834,385

[22] Filed: Apr. 16, 1997

[30] Foreign Application Priority Data

Apr. 16, 1996 [JP] Japan .................................. 8-093828

[51] Int. Cl.⁶ .............................. C12Q 1/68; C12P 19/34; C07H 21/02; C12N 15/00
[52] U.S. Cl. ........................... 435/6; 435/91.2; 536/23.1; 536/24.3; 935/76; 935/77; 935/78
[58] Field of Search .................... 435/6, 91.2; 935/76, 935/77, 78; 536/23.1, 24.3

[56] References Cited

U.S. PATENT DOCUMENTS

| | | | |
|---|---|---|---|
| 5,043,272 | 8/1991 | Hartley | 435/91 |
| 5,496,699 | 3/1996 | Sorenson | 435/6 |
| 5,604,097 | 2/1997 | Brenner. | |
| 5,650,274 | 7/1997 | Kambara et al.. | |
| 5,654,413 | 8/1997 | Brenner. | |

OTHER PUBLICATIONS

Elsevier Science B.V. "Fragment Walking for Long DNA Sequencing by Using a Library as Small as 16 Primers" Gene 176 (1996) pp. 231–235.
K. Murakawa, et al., Genomics, 23 379–389 (1994).
Y. Hayashizaki, et al., DNA Polymorphism, 3, 10–15 (1995).
S. Sugano, et al., Protein, Nucleic Acid and Enzyme, 38(3), 276–281 (1993).
Sambrook, et al., Molecular Cloning a Laboratory Manual, 2nd edition, 7.1–7.36 (1987) (Cold Spring Harbor Laboratory Press).

U.S. Patent Application filed Nov. 27, 1996 based on Japanese Application No. 7–311949 of Kambara, et al.

*Primary Examiner*—W. Gary Jones
*Assistant Examiner*—Ethan Whisenant
*Attorney, Agent, or Firm*—Antonelli, Terry, Stout & Kraus, LLP

[57] ABSTRACT

The present invention comprises a method for analysis of a nucleic acid which comprises:

(1) a step of digesting a double-stranded DNA sample with a plurality of restriction enzymes to obtain double-stranded DNA fragments;

(2) a step of ligating a plurality of oligonucleotides to the double-stranded DNA fragments respectively at the both ends thereof;

(3) a step of dispensing a solution containing the double-stranded DNA fragments into a plurality of tubes;

(4) a step of adding DNA primers comprising combinations of DNA primers selected from each set of a plurality of DNA primer sets comprising a plurality of labeled primers having a base sequence complementary to the base sequence of oligonucleotide and a part or all of the base sequence contiguous to the base sequence complementary to the base sequence of the oligonucleotide and recognized by the restriction enzymes and a selective base sequence of 1 to 4 bases at the 3'-end thereof, to the respective tubes corresponding to the combinations and performing a complementary strand synthesis reaction of the region of the double-stranded DNA fragments between the base sequences recognized by the two restriction enzymes; and, (5) a step of subjecting the products obtained by the complementary strand synthesis reaction to electrophoresis to produce a large number of DNA fragments from the long double stranded DNA sample digested with restriction enzymes and obtain fingerprinting patterns therefrom which enables to inspect the long double-stranded DNA sample.

21 Claims, 5 Drawing Sheets

FIG. 5 ively as a whole. Where DNA functions in vivo, DNA information is initially transcribed onto mRNA, in which a protein is synthesized to make a living organism function. Noting this function, an attempt has been made in, e.g., the cDNA project to which attention has been brought in the genome project, to explore the function of the living organism based on information of the kind and amount of cDNA by producing cDNA from mRNA.

According to the cDNA project, cDNAs complementary to mRNAs expressed in cells are separated for sequencing of each cDNA, whereby frequency of the base sequence of cDNA appearing in one tissue is determined. For the determination, cDNAs are converted from mRNAs (in which various cDNAs are present in admixture) and the desired cDNAs are cloned. *Escherichia coli* with the cDNAs is spread over agar medium and cultured to obtain colonies. The respective colonies contain any one of the desired cDNAs. After the cDNA is collected from the corresponding colony, its base sequence is determined to identify the kind of cDNA. During the course of identifying the kind of cDNA in each colony in such a manner, the same kind of cDNA is detected. When a particular cDNA is present in a larger amount in one tissue, it means that the cDNA corresponds to a gene strongly expressed in that tissue, indicating its appearance with high frequency in the colony. Thus, cDNA sequencing is performed in a number of colonies to determine what cDNA appears how frequently (K. Murakawa et al., Genomics, 23, 379–389 (1994)).

On the other hand, an attempt has also been made to effect DNA diagnosis, noting the genome (all chromosomal DNAs) or a particular chromosome as a whole, which is called gene scanning or restriction landmark genome scanning (Y. Hayashizaki et al., DNA Polymorphism, 3, 10–15 (1995), published by Toyo Shoten). In the gene scanning, DNA is digested with a first restriction enzyme (e.g., 8-base recognition restriction enzyme such as Not I, etc., with which DNA is digested by once per 64 kb in average), and a radioisotope-tagged or fluorophore-tagged nucleotide is ligated with the digestion site, which is then subjected to electrophoresis on agarose gel toward a first direction. After separating the migrated pattern, the DNA fragment on the agarose gel is further digested with a second restriction enzyme (e.g., 4-base recognition restriction enzyme with which DNA is so digested by once per 256 bases in average), which is again subjected to electrophoresis toward a second direction intersecting to the first direction to obtain 2-dimensional migration pattern. The 2-dimensional migration pattern is utilized as a fingerprint to examine the full length DNA. Since DNA in cells with abnormality such as cancer, etc. has a different 2-dimensional pattern from DNA in normal cells, an attempt has been made to utilize the difference for diagnosis. However, it is the actual situation that there is no effective method to specify the location of abnormality in a long DNA.

As described above, it is of particular importance for understanding of the function of DNA displayed in cells to analyze a long DNA or appreciate and inspect the entire profile of a sample containing a plurality of DNAs for early identification of disease. However, any good measure is unknown in the prior art. Speaking of conventional cDNA analysis technology, it is required to determine a large number of base clones in a sample, resulting in much labor and time so that a problem encounters that conventional cDNA analysis is not practical for applying its technology to various samples. Furthermore, a method using conventional DNA probes is only available for single analysis of, at most, several to several tens of DNAs but is unsuitable for inspection of cDNAs or DNA fragments amounting to several hundreds to even several ten hundreds. The method further involves an additional problem that it is not available for inspection of such a long DNA that abnormality cannot be located.

On the other hand, DNA having a long base length can be analyzed by conventional gene scanning. However, the gene scanning also involves problems that a large volume of sample DNA is required, a considerable amount of a second restriction enzyme is required to digest the DNA fragment separated toward the first direction through electrophoresis, the mobility of each DNA fragment in the 2-dimensional migration pattern is not always quantitative in the two directions of electrophoresis to fail accurate determination of the length in each DNA fragment separated by 2-dimensional electrophoresis, resulting in difficulty to use as a database as fingerprints.

SUMMARY OF THE INVENTION

An object of the present invention is to provide a novel fingerprinting method or a method for analysis of DNA which overcomes the foregoing problems observed in the prior art.

In the present invention, the method typically comprises the following steps. First, a double-stranded DNA used as a sample is digested with at least two restriction enzymes to produce a group of double-stranded DNA fragments inherent to the sample DNA which have a plurality of lengths. An oligonucleotide having a known base sequence is ligated to double-stranded DNA fragment respectively at the both 3'-ends (termini) thereof, thereby to provide an area to which a part of the DNA primer can hybridize. There are prepared a plurality of DNA primer sets which hybridize to the area and the recognition sequence by the restriction enzymes used and several bases adjacent thereto. In the DNA primer sets, 1 to 3 bases of each primer at the 3'-end constitute a selective base sequence for discriminating 1 to 3 bases adjacent to the recognition sequence of each DNA fragment by the corresponding restriction enzyme and the selective base sequence includes the combinations of substantially all bases (A, T, G and C). The number of restriction enzymes used is the same as the number of the DNA primer sets prepared. Double-stranded DNA fragments are dispensed into the number of the combinations of primers in the DNA primer sets. A combination of different primers is added to each fraction to cause hybridization, whereby complementary strand synthesis is performed. Each primer in the DNA primer set is labeled with a marker such as a fluorophore. The reaction products of the complementary strand synthesis obtained in the respective fractions are separated in different lanes by gel electrophoresis. The length of each DNA fragment is measured to obtain a fingerprint.

Where a group of the double-stranded DNA fragments contains a large number of DNA fragments, it is often difficult to discriminate their lengths. Even in such a case, most DNA fragments have different base sequences adjacent to the restriction enzyme site. Thus, the DNA fragments are classified, taking advantage of the difference in base sequence adjacent to the restriction enzyme site. For classification of the DNA fragments, complementary strand synthesis is conducted using 4 to 64 kinds of DNA primers having base sequences of the 3' terminal 1 to 3 bases in all combinations. Where the terminal 2 to 3 bases from DNA primers completely hybridize to DNA fragments, complementary strand synthesis proceeds but otherwise does not.

Where double-stranded cDNA is prepared from mRNA, mRNA is hybridized at the 3'-end thereof with biotinylated oligo dT primer and then reacted with reverse transcriptase and DNA polymerase to prepare double-stranded cDNA. Alternatively, the double-stranded cDNA may be prepared in a similar manner, after introducing biotin into the terminus of cDNA corresponding to the 5' end of mRNA utilizing a cap structure. The double-stranded cDNA is divided into two fractions and the first or second restriction enzyme is added to the respective fractions to digest the double-stranded cDNA. After the fragments other than biotinylated fragments are removed, the first or second oligonucleotide is ligated to the digested DNA termini, respectively.

For redigestion, the second restriction enzyme is then added to the fraction added with the first restriction enzyme and, the first restriction enzyme is added to the fraction added with the second restriction enzyme. The first or second oligonucleotide is ligated to the digestion sites, respectively. When the biotinylated fragments are removed, the both ends are digested with the first and second restriction enzymes to form the DNA fragments ligated to the first and second oligonucleotides. That is, the both ends of the resulting fragments are digested with different restriction enzymes. When complementary strand synthesis is carried out using the combination of labeled primers in each of the DNA primer sets, which hybridize to a part or all of the recognition sequence with each restriction enzyme, the reaction occurs only in the DNA fragments in which the terminal bases of the primer hybridize, among the DNA fragments, both ends of which are digested with different restriction enzymes.

The thus obtained DNA strand by complementary strand synthesis has substantially the same length as that of the original DNA fragment strand. Accordingly, the length of the DNA strand can be measured by means of, e.g., gel electrophoresis. Where the DNA fragments synthesized only by single complementary strand synthesis does not meet a detection sensitivity, the complementary strand synthesis can be repeated using thermostable DNA polymerase to amplify the amount of the DNA fragments produced. In this case, the terminal base sequence of primers may be modified to control the degree of complementary strand synthesis. This 3'-terminal base sequence is called a selective base sequence. By using primers having a selective base sequence and complementary to the first and second oligonucleotides, only a particular DNA fragment can be selectively amplified. For example, when two bases are employed as a selective base sequence, DNA fragments can be classified into $4^2 \times 4^2 = 256$ groups. The DNA fragments classified into 256 groups are electrophoresed in different lanes depending upon group to obtain fingerprinting patterns.

According to the present invention, a sample DNA is digested with at least two restriction enzymes, complementary strand synthesis is conducted using definite DNA primer sets, the resulting DNA fragments are amplified, a large number of the DNA fragments are classified into groups, the number of the DNA fragments in the respective groups is reduced, electropherograms of the DNA fragments in each group are obtained and the construction of the sample DNA can be determined by comparison of the electropherogram, as described above. The present invention provides advantages that by digesting a sample DNA with at least two restriction enzymes, the base sequences of DNA fragments at the both ends thereof can be clearly identified and the length of each fragment can be specified and moreover, the number of groups for classification of the DNA fragments can be increased. When the number of the selective base sequences of primers for discriminating the terminal sequences of DNA fragments is, e.g., 3 bases, the DNA fragments can be classified into $4^3 = 64$ groups. When two DNA primer sets of the primers having selective base sequences in 64 combinations, the DNA fragments can be classified into groups of $64 \times 64 = 4096$. In terms of dissolution power in gel electrophoresis, more than 100 types of DNA fragments per fraction can be discriminated. Thus, the 4096 groups classified as above can discriminate DNA fragments of more than 4096'100≈400,000. According to the present invention, a fingerprinting pattern can be obtained from a large number of DNA fragments obtained by digestion of a long nucleic acid with restriction enzymes, that enables to analyze or evaluate the long nucleic acid.

DESCRIPTION OF THE PREFERRED EMBODIMENTS

Hereinafter the method for analysis of nucleic acid according to the present invention will be described in detail with reference to the drawings.

The method of the present invention provides a fingerprinting technique which enables to assay a long nucleic acid.

EXAMPLE 1

Figure 1:
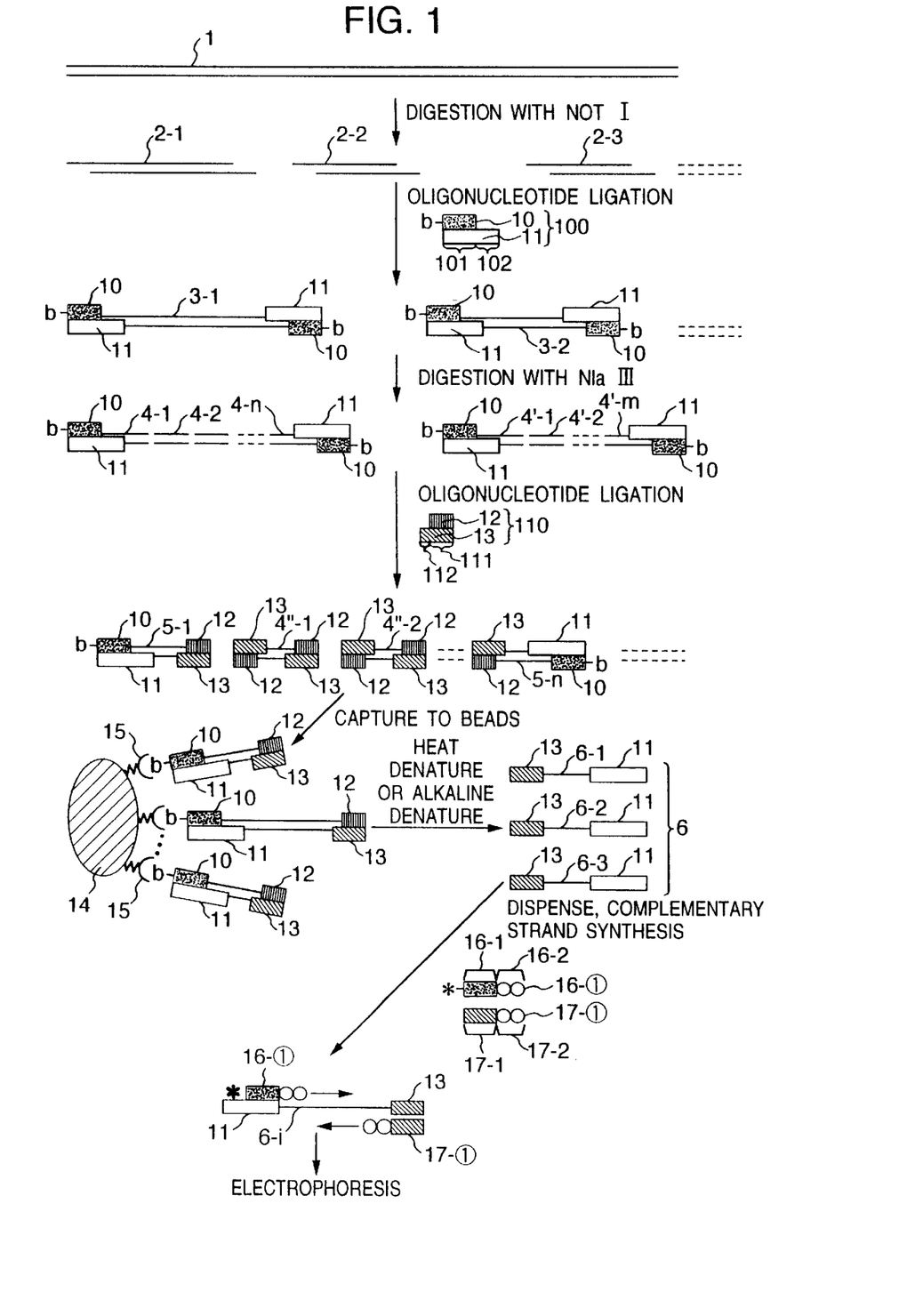
FIG. 1 is a chart for explaining the procedures of Example 1 of the present invention which indicates the procedures for producing a mixture of DNA fragments from a sample DNA and then performing complementary strand synthesis to obtain DNA fragments.

FIG. 1 is a chart for explaining the procedures of obtaining a DNA fragment which comprises producing a mixture of DNA fragments from a sample DNA using a plurality of restriction enzymes and performing complementary strand synthesis using first and second primer sets. The thus obtained DNA fragment has at the 5'-end thereof a desired base sequence of two bases adjacent to the base sequence complementary to all of the recognition sequences of the restriction enzymes or to a part of the recognition sequences at the 3'-end thereof. In Example 1, *Escherichia coli* genomic DNA 1 (up to 5 Mb) is used as sample DNA. The recognition sequence of Not I, which is a 8-base recognition restriction enzyme and recognizes a base sequence of GCGGCCGC, appears once per 64 kb in average. Thus, digestion of *E. coli* genomic DNA 1 with Not I produces approximately 100 double-stranded DNA fragments 2-1, 2-2, 2-3, . . . . A double-stranded biotinylated oligonucleotide 100 (having a known base sequence) is ligated to the both ends (namely, the sites digested with Not I) of the double-stranded DNA fragments 2 produced to obtain DNA fragments 3-1, 3-2, . . . (for brevity, biotin is shown by symbol "b" in each of the following figures). The double-stranded biotinylated oligonucleotide (first oligonucleotide) 100 consists of single-stranded oligonucleotide 10 (preferably having a base length of 10 to 30), which is biotinylated at the 5'-end thereof, and single-stranded oligonucleotide 11 having at the 5'-end thereof all or part of base sequence 101 complementary to the oligonucleotide 10 and base sequence CGCCGGCG 102 complementary to the base sequence recognized by Not I.

Next, DNA fragments 3-1, 3-2, . . . are further digested with restriction enzyme NlaIII, which is a 4-base recognition restriction enzyme and recognizes base sequence CATG, appears once per 256 bases in average. Thus, each of the DNA fragments 3-1, 3-2, . . . is digested with the restriction enzyme around the both ends thereof. A second double-stranded oligonucleotide 110 (having a known base sequence) is ligated to the both ends (namely, the sites digested with NlaIII) of the double-stranded DNA fragments 4-1, 4-2, . . . 4-n, 4'-1, 4'-2, . . . , 4'-m. The second double-stranded oligonucleotide 110 consists of single-stranded oligonucleotide 12 (preferably having a base length of 10 to 30) and single-stranded oligonucleotide 13 having at the 5'-end thereof all or part of base sequence 111 complementary to the oligonucleotide 12 and base sequence GTAC 112 complementary to the base sequence recognized by NlaIII. Thus, the DNA fragments 4"-1, 4"-2, . . . having the second oligonucleotide 110 at the both ends thereof and the DNA fragments 5-1, 5-2, . . . having the first oligonucleotide 100 at one end and the second oligonucleotide 110 at the other end are produced.

From these products, the DNA fragments 5-1, 5-2, . . . 5-n bearing the first oligonucleotide 100 at one end and at the other end the second oligonucleotide 110 are captured to avidin 15 bound to beads 14. The number of the thus obtained fragments is approximately 200 in total, since one fragment produced by digestion with Not I is further digested around the both ends thereof to obtain two fragments.

Subsequently, the captured fragments are heat-denatured or alkaline-denatured to dissociate biotin (b)-free complementary strands (DNA fragments) 6 (6-1, 6-2, 6-3, . . . ). The thus obtained complementary strands 6 are fragments respectively (1) having at the 3'-end thereof having at the 5'-end thereof the single-stranded oligonucleotide 11 having the base sequence 101 complementary to the oligonucleotide 10 and the base sequence (CGCCGGCG) 102 complementary to the base sequence recognized by Not I, and (2) having at the 5'-end thereof single-stranded oligonucleotide 13 having at the 5'-end thereof the base sequence 111 complementary to the oligonucleotide 12 and the base sequence (GTAC) 112 complementary to the base sequence recognized by NlaIII.

There is prepared a first DNA primer set consisting of primers 16-①, 16-②, . . . , which contains base sequence 16-1 of the full-length Not I recognition sequence or a part of the 3'-terminal Not I recognition sequence and selective sequence 16-2 of two bases adjacent to the base sequence 16-1 (the base sequence 16-① is only shown in FIG. 1). The first DNA primer set 16 comprises 16 primers having different base sequences of the 3' terminal 2-base selective sequences. That is, the base sequences of the 3'-terminal 2-base selective sequences are 4×4=16 combinations which correspond to all combinations of 2 bases selected from A, T, G and C. Likewise, there is prepared a second DNA primer set of primers 17-①, 17-②, . . . , which contains base sequence 17-1 of the full-length NlaIII recognition sequence or a part of the 3'-terminal NlaIII recognition sequence and selective sequence 17-2 of two bases adjacent to the base sequence 17-1 (only the base sequence 17-① is shown in FIG. 1). The second DNA primer set also consists of 16 primers having different base sequences in the 3'-terminal 2-base selective sequences, as in the first DNA primer set. Each primer of the first DNA primer set 16 is labeled with a fluorescent tag (which is designated with *) at the 5'-end thereof.

A solution containing complementary strand 6 is dispensed in 256 tubes (not shown). One primer selected from the first DNA primer set 16 and one primer selected from the second DNA primer set 17 are added to the 256 tubes, respectively. Selection of the kind of primers from the first and second DNA primer sets is made in 16×16=256 combinations in total of the primers in the first and second DNA primer sets. Two kinds of primers selected from different combinations are added to each of the tubes. That is, 16 kinds of primers are in the first and the second primer sets and hence, the primers have 16×16=256 combinations in total. In the 256 combinations of the primers, complementary strand synthesis of complementary strand 6 is performed in 256 tubes (for brevity, only one tube is shown in FIG. 1). In the complementary strand synthesis, extension proceeds on DNA fragment 6-i (−strand) using primer 16-① of the first DNA primer set to produce double strands. The double strands are heat-denatured. Complementary strand synthesis proceeds on the resulting single +strand and −strand using primer 17-① of the second primer set and primer 16-① of the first primer set, respectively, to form double strands. The thus obtained complementary strand synthesis products are electrophoresed to obtain electropherograms. In the electrophoresis using denaturing polyacrylamide gel, the complementary strand synthesis products in the 256 tubes are electrophoresed in a single-stranded state onto 256 lanes corresponding to the tubes. Where four different fluorescent labels are used for labeling each primer at the 5'-end in the first DNA primer set 16, complementary strand synthesis using primers of the first DNA primer set having four different fluorescent label can be carried out in the same tube. Complementary strand synthesis products in 64 tubes can be electrophoresed in a single-stranded form into 64 lanes corresponding to the tubes.

Figure 2:
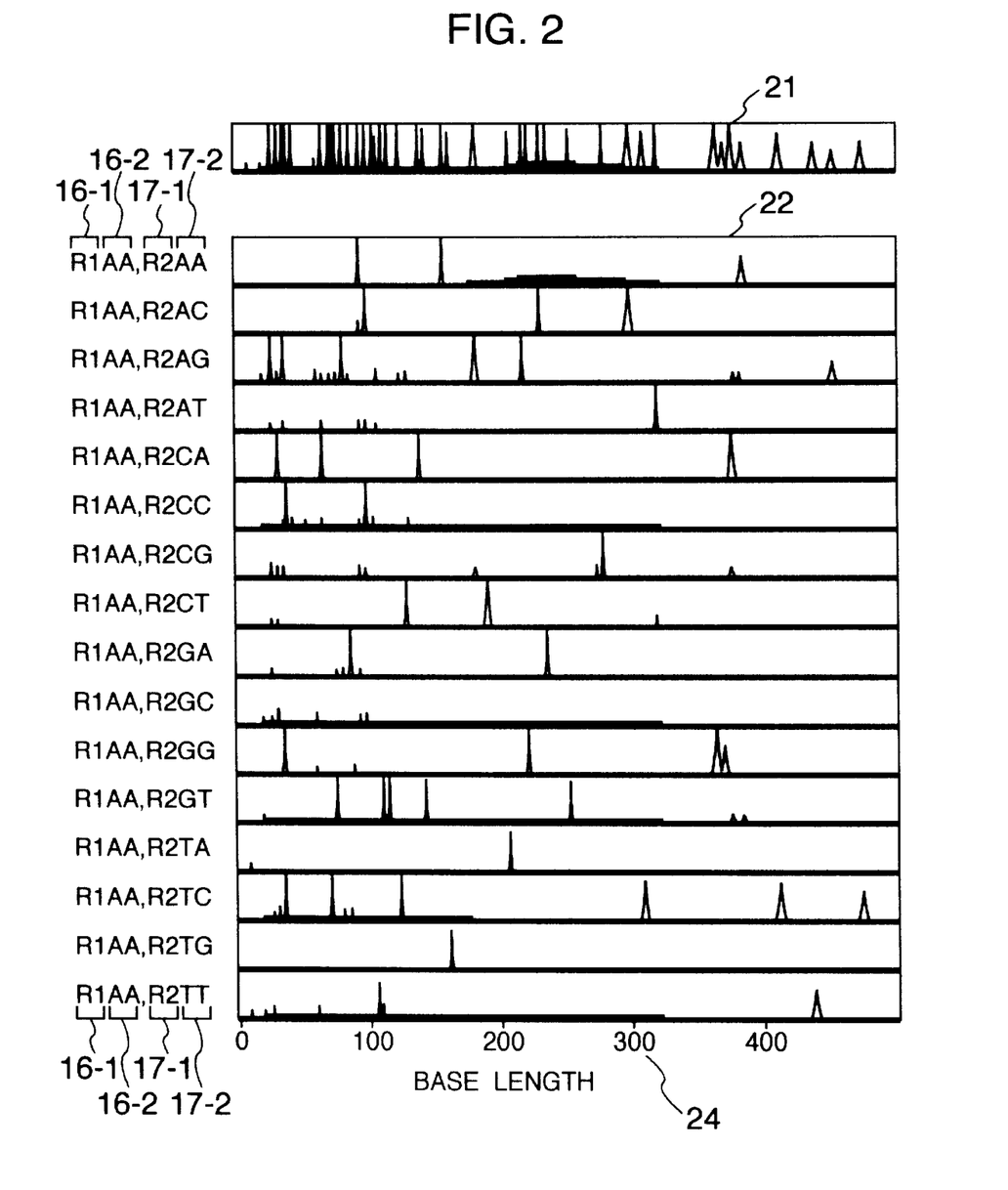
FIG. 2 shows a part of electropherograms of the DNA fragments in the products by complementary strand synthesis in Example 1 of the present invention.

FIG. 2 shows a part of gel electropherograms of the DNA fragments in the products by complementary strand synthesis described above. In FIG. 2, 21 designates an electropherogram obtained by simultaneous electrophoresis of all DNA fragments from the complementary strand synthesis products described above; 22 designates an electropherogram obtained by electrophoresis of the DNA fragments in each tube of the complementary strand synthesis products described above; 16-2 and 17-2 designate base sequences in the selective base sequences of the primers employed; and 24 designates base length of DNA fragments. In FIG. 2, symbols R1 and R2 designate the base sequences of 16-1 at the 5'-ends of primers 16-①, 16-②, . . . in the first DNA primer set 16 and the base sequences of 17-1 at the 5'-ends of primers 17-①, 17-②, . . . in the second DNA primer set 17, respectively. When the lengths of all DNA fragments are simultaneously measured in the same lane, many peaks overlap with each other as shown in electropherogram 21 and each DNA fragment cannot be discriminated, which makes analysis impossible. Pattern 22 indicates an electropherogram obtained by the steps of modifying the combinations of two bases 16-2 and 17-2 in the selective base sequences (which discriminate each DNA fragment) of primers in the first and second DNA primer set; performing complementary strand synthesis; discriminating the base sequences at the ends of the DNA fragments; and subjecting the DNA fragments to gel electrophoresis in different lanes for each combination of the selective base sequences 16-2 and 17-2. Since the DNA fragments are discriminated and electropherogram is obtained for each combination of selective base sequences 16-2 and 17-2, the peaks are separated from each other so that the length of the DNA fragment (base length of 24) contained in the electropherogram can be appreciated. In the case of Example 1, complementary strand synthesis is carried out using 256 combinations of the primers in the first and second DNA primer sets, 256 patterns of electropherograms can be obtained. However, the electropherogram of each DNA fragment is inherently possessed by the intact DNA sample. Where the DNA sample is different, another pattern is obtained so that this is applicable widely for diagnosis of DNA, etc. That is, by a plurality of combinations of the selective base sequence in the primers of the first and second DNA primer sets (in FIG. 2, one selective base sequence is fixed to be AA and other selective base sequences are modified into 16 sequences of AA, AC, AG, . . . TG and TT), sample DNA can be analyzed more accurately. In Example 1, DNA fragments 4"-1, 4"-2, . . . and DNA fragments 5-1, 5-2, . . . may be further digested with restriction enzyme MboI (which is a 4-base restriction enzyme and recognizes base sequence GATC), after DNA fragments 4"-1, 4"-2, . . . and DNA fragments 5-1, 5-2, . . . . In this case, a third double-stranded oligonucleotide may or may not be ligated to DNA fragments at the both ends, which are obtained by digestion with restriction enzyme MboI. Where DNA fragment is further digested with a third restriction enzyme as described above, for example, where DNA fragments 5-1, . . . , 5-n shown in FIG. 1 are digested with a third restriction enzyme, no double-stranded DNA fragment is obtained in FIG. 1, even though complementary strand synthesis is performed. Thus, electropherogram of the complementary strand synthesis products is simplified, which results in effects that fingerprinting pattern can be readily discriminated and a sample can be analyzed more accurately.

EXAMPLE 2

Example 2 is an embodiment in which the method of the present invention is applied to analysis of mRNA.

Figure 3:
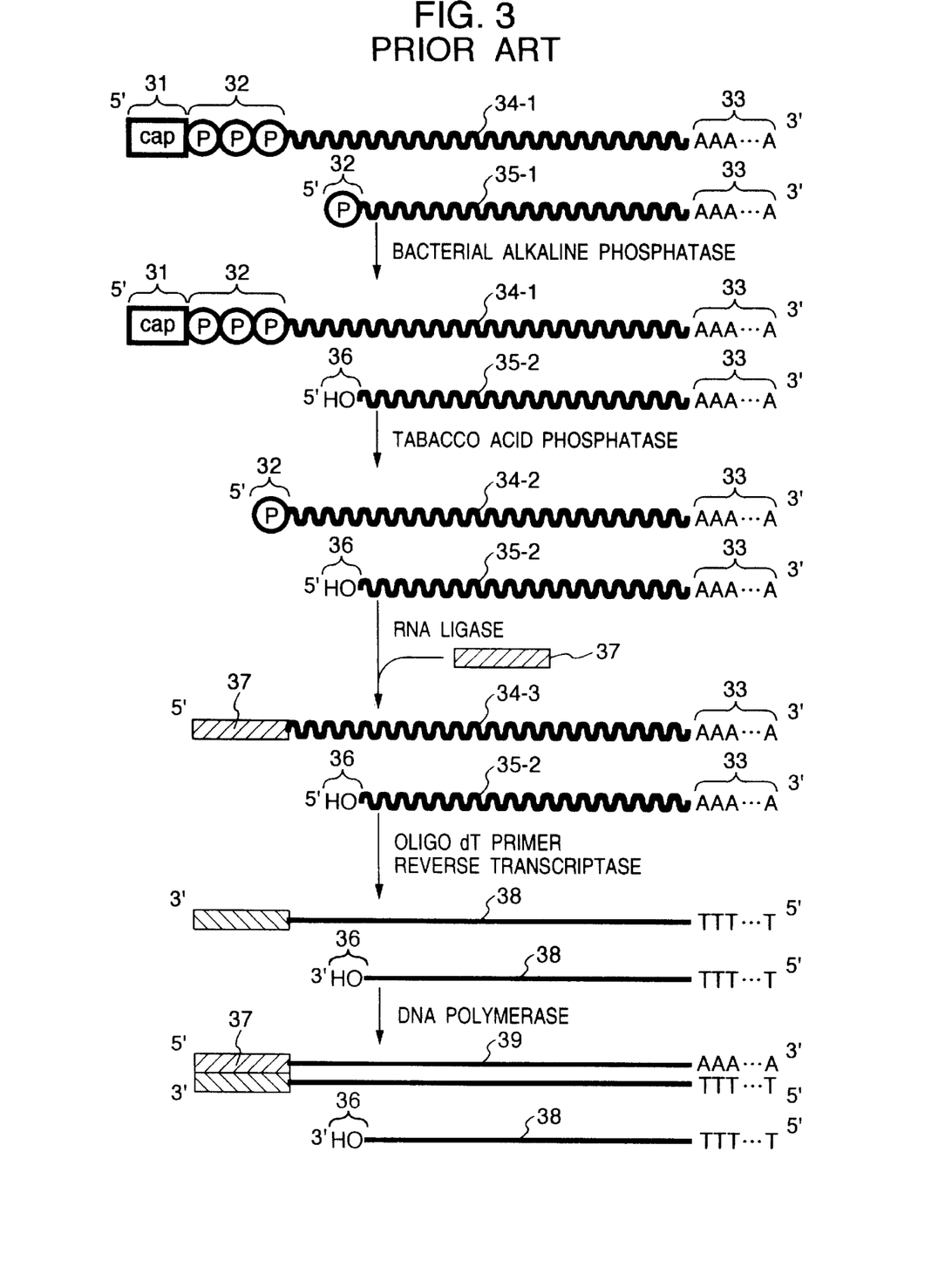
FIG. 3 is a chart for explaining the procedures of a reaction in the prior art by synthesizing double-stranded cDNA from mRNA to obtain a sample DNA, which is used in Example 2 of the present invention.
Figure 4:
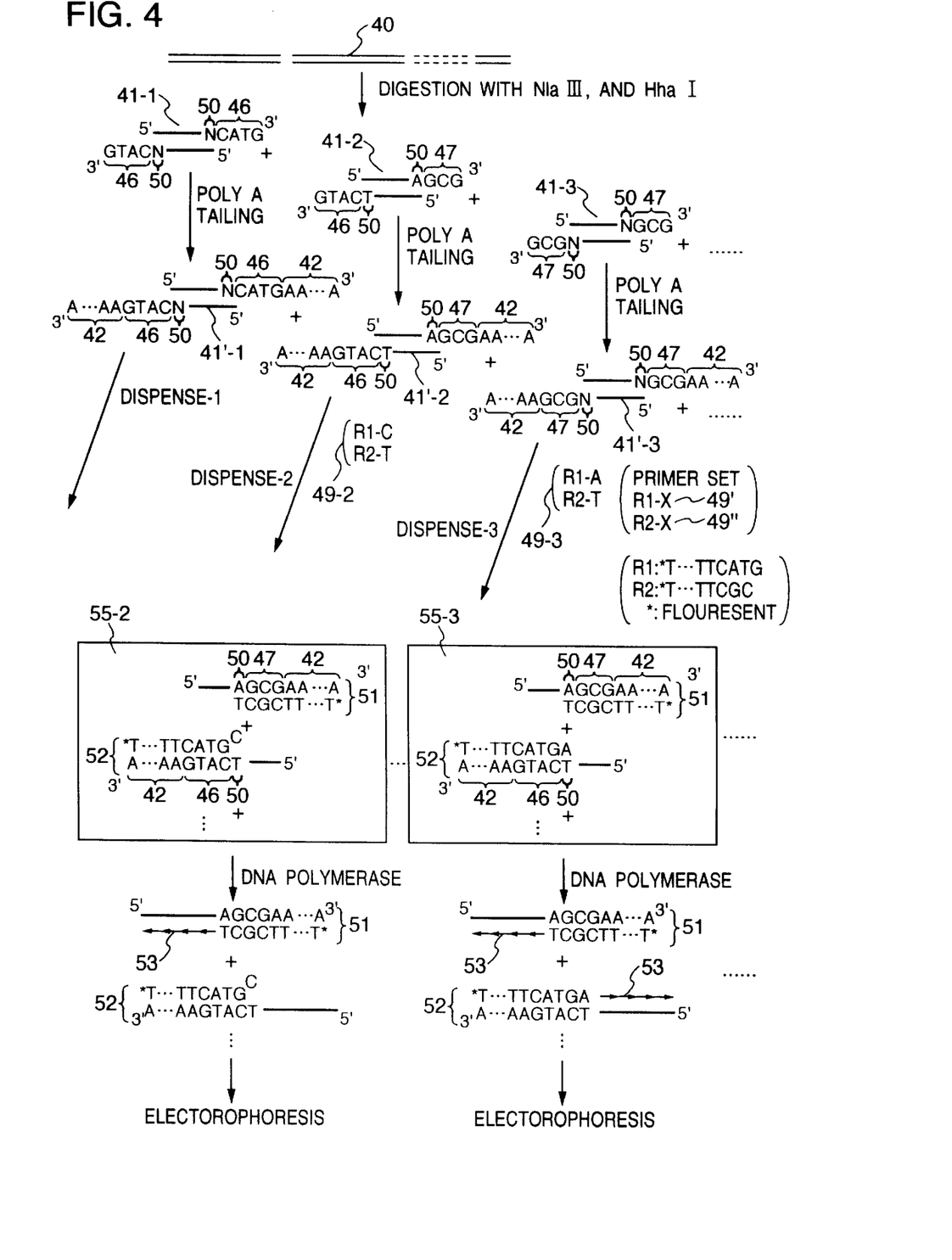
FIG. 4 is a drawing for explaining the procedures in Example 2 of the present invention, in which a mixture of double-stranded cDNAs is digested with two different restriction enzymes followed by complementary strand synthesis to obtain DNA fragments.

FIG. 3 is a chart for explaining the procedures of a reaction in the prior art by synthesizing double-stranded cDNA from mRNA to obtain a sample DNA, which is used in Example 2 of the present invention. FIG. 4 is a drawing for explaining the procedures in Example 2 of the present invention, in which a mixture of double-stranded cDNAs is digested with two different restriction enzymes followed by complementary strand synthesis to obtain DNA fragments having at the 5'-end thereof a base sequence of definite one base contiguous to the recognition sequences with the restriction enzymes.

FIG. 3 is a chart for explaining the procedures of a reaction for synthesizing double-stranded cDNA from mRNA to obtain a sample DNA, which is used in Example 2 of the present invention and described in the prior art, PROTEIN, NUCLEIC ACID AND ENZYME, vol. 38, No. 3, 276–281 (1993) published by Kyoritsu Publishing Co., the content of which is incorporated hereinto by reference. As shown in FIG. 3, mRNA extracted from cells contains full-length mRNA 34-1 having polyA tail 33 at the 3'-end thereof and cap structure 31 and phosphate group 32 at the 5'-end thereof, and non-full-length mRNA 35-1 having phosphate group 32 at the 5'-end thereof. First, mRNAs 34-1 and 35-1 are treated with bacterial alkaline phosphatase to remove the 5'-terminal phosphate group 32 in the non-full-length mRNA 35-1 having no cap structure, whereby mRNA 35-1 is converted into the structure 35-2 having hydroxyl group 36 at the 5'-end thereof.

The mRNA 35-2 is then treated with tobacco acid pyrophosphatase to expose the phosphate group 32 only at the 5'-end of full-length mRNA 34-1 having a cap structure and convert mRNA 34-1 into structure 34-2 having the phosphate group 32 exposed at the 5'-end thereof. Synthetic RNA oligonucleotide 37 is introduced into the 5'-end of mRNA 34-2 using RNA ligase to obtain RNA oligonucleotide-ligated mRNA 34-3. RNA ligase has the function to ligate RNA oligonucleotide to the RNA having a phosphate group at the 5'-end but not to the RNA having a hydroxyl group at the 5'-end. Therefore, the synthetic oligonucleotide is ligated only to full-length mRNA 34-2.

After synthetic oligonucleotide 37 is ligated only to the full-length mRNA 34-1 as described above, the mRNA is converted into cDNA 38 using oligo dT primer and reverse transcriptase. Using DNA polymerase, the second strand of cDNA 38 is further synthesized to obtain, as a double-stranded DNA sample 40, a mixture of double-stranded cDNAs 39 corresponding to various mRNAs extracted from cells.

FIG. 4 is a chart for explaining the procedures which comprises digesting the double-stranded cDNA sample with two different restriction enzymes and performing complementary strand synthesis using two DNA primer sets to obtain DNA fragments having at the 5'-end thereof a base sequence of definite one base contiguous to the recognition sequences with the restriction enzymes. Needless to say, the procedures shown in FIG. 4 are also applicable to a single long double-stranded DNA sample. First, the double-stranded DNA sample 40 comprising a mixture of double-stranded cDNAs is digested with restriction enzymes NlaIII and HhaI. Restriction enzymes NlaIII and HhaI digest double-stranded DNA as shown by CATG- or GCG-C. The 3'-end of each fragment produced by the digestion becomes CATG (NlaIII-digested end) 46 when digested with NlaIII and GCG (HhaI-digested end) 47 when digested with HhaI. Numeral 50 designates one base at the 5'-end contiguous to each of the recognition sites with the restriction enzymes (NlaIII-digested end, HhaI-digested end) and symbol N designates any one of A, T, G and C. Either oligonucleotide is introduced into each of DNA fragments 41-1, 41-2, 41-3, . . . , at the 3'-end thereof through ligation, or polyN tailing (any one of polyA tail, polyC tail, polyG tail and polyT tail) is added to each of the DNA fragments at the 3'-end thereof using terminal deoxynucleotidyl transferase. Hereinafter the embodiment in which polyA tail 42 is added to the DNA fragments is explained by way of a typical example.

When polyA tail 42 is added to the 3'-end of each DNA fragment, the 3'-terminal base sequence digested with NlaIII becomes CATGAA . . . A3' as shown in 41'-1 and 41'-2. Likewise the 3'-terminal base sequence of the DNA fragment digested with HhaI becomes GCGAA . . . A 3' as shown in 41'-2 and 41'-3.

Two DNA probe (primer) sets 49'and 49" are prepared. Each primer of DNA primer sets 49' and 49" is labeled with a fluorescent tag, etc. A first DNA primer set (R1–X, R1=*T . . . TTCATG, wherein symbol * designates a fluorescent label) of four primers having base sequences of 5'T . . . TTCATGX 3' (wherein X is A, C, G or T) is prepared as primers which can hybridize to the digestion site with NlaIII. As primers that can hybridize to the digestion site with HhaI, there is prepared a second DNA primer set (R2–X, R2=*T TTCGC, wherein symbol * designates a fluorescent label) of four primers having base sequences of 5' T TTCGCX 3' (wherein X is A, C, G or T).

The base sequence from the 5'-end to CATG of the primers in the first DNA primer set is complementary to all of the DNA fragments digested with NlaIII and thus hybridizes to the end of the DNA fragments digested with NlaIII. However, the base sequence X hybridizes only to the fragment having a base sequence complementary to the base X. Where X is, e.g., A, the base X hybridizes only to fragments having complementary base T in the site 50 of base N. Where the site 50 in base N is not a complementary base, the site of base N does not hybridize as in 52. Likewise, the base sequence from the 5'-end to CGC of the primers in the second DNA primer set is complementary to all of the DNA fragments digested with HhaI and thus hybridizes to the end of the DNA fragments digested with NlaIII. However, the base sequence X hybridizes only to the fragment having a base sequence complementary to the base X. It is not clearly seen only from stability of hybridization if the base X completely hybridizes. This is because almost all sites of the DNA primers possess a common sequence that can hybridize to any fragment and hence, any difference in stability of hybridization only at the terminal several base portions is not large enough to determine complete hybridization. However, it can be verified by complementary strand synthesis using DNA polymerase if the terminal bases completely hybridize.

A solution containing the DNA fragments digested with the two restriction enzymes and added with polyA tail 42 at the 3'-end thereof is dispensed into 16 fractions 55 (fractions 55-2 and 55-3 out of 55-1, 55-2, . . . , 55-16 are only shown in FIG. 4). In the 16 fractions of 55-1, 55-2, . . . , 55-16, two primers out of 16 different combinations of the primers from the first DNA primer set 49' (R1–X wherein X=A, C, G or T) and the primers from the second DNA primer set 49" (R2–X wherein X=A, C, G or T) are added to the 16 fractions corresponding to 16 combinations to perform complementary strand synthesis. In FIG. 4, two primers 49-2 (R1–C, R2–T) added to fraction 55-2 and two primers 49-3 (R1–A, R2–T) added to fraction 55-3 are shown. The primers hybridize to the DNA fragments, wherein only the primers that completely hybridize at the both 3'-ends thereof as in 51 (in which the site of base N completely hybridizes) undergo complementary strand synthesis to form their extended complementary strands. The primers as in 52 (in which the site of base N does not hybridize) that hybridizes only at one 3'-end thereof do not undergo complementary strand synthesis so that no extended complementary strand is formed.

Where both strand of primers completely hybridize at the both 3' ends thereof by conducting the complementary strand synthesis in an n cycle, the complementary strand 53 having the same length as that of the DNA fragment is amplified by 2n times. Where only the first strand of the primer completely hybridizes at the 3'-end thereof (52), the complementary strand is amplified only by n times even though complementary strand synthesis is repeated in an n cycle. Thus, complete hybridization at the both 3' ends can be readily distinguished over the complete hybridization only at the one 3' end. The primers are labeled with, e.g., a fluorescent tag so that the length of the extended complementary strand can be determined by a fluorescent DNA sequencer.

Thereafter, as in the case of Example 1, the products obtained by complementary strand synthesis of the respective fraction are electrophoresed in different lanes, namely, in different lanes corresponding to the combination of primers. By comparing electropherograms, the sample DNA can be analyzed. In this case, there are 4×4=16 combinations of the primers so that electropherograms of 16 DNA fragments are obtained. The spectrum of each DNA fragment is inherently possessed by intact mRNA and thus applicable not only to the analysis but also to diagnosis of mRNA. Where different four kinds of labels are employed as fluorescent labels of the 5'-end of each primer of the first DNA primer set, complementary strand synthesis using the primers having different four fluorescent labels from the first DNA primer set can be carried out in the same tube. The products obtained by complementary strand synthesis performed in 4 tubes can be electrophoresed in a single-stranded form in four lanes corresponding to the tubes.

In a further embodiment of Example 2, double-stranded sample DNA may also be digested with three restriction enzymes; and complementary strand synthesis is then carried out using three DNA primer sets to obtain DNA fragments having a base sequence containing one definite base at the 5'-end thereof contiguous to the recognition sequences by the restriction enzymes. In this case, a third DNA primer set in addition to the first and second DNA primer sets (R1–X, R2–X wherein X is A, T, G or C). A solution containing the DNA fragments obtained by digestion with the three restriction enzymes and added with polyA tail 42 at the 3'-end thereof is dispensed in 48 fractions, which correspond to the total number in combinations of the primers with fluorescent tags from the first, second and third DNA primer sets (R1–X, R2–X and R3–X, wherein X is A, T, G or C), that is, 16 combinations from R1–X and R2–X, 16 combinations from R1–X and R3–X, and 16 combinations from R2–X and R3–X. Thereafter the fractions are treated in a similar manner. The products obtained from the respective fractions by complementary strand synthesis are electrophoresed in different 48 lanes, that is, in different lanes corresponding to every combination of the primers. By comparing the resulting electropherograms, sample DNA can be analyzed. In this case, there are 48 combinations of the primers so that electropherograms of 48 DNA fragments are obtained. The spectrum of each DNA fragment is inherently possessed by intact mRNA and thus applicable not only to a detailed analysis of mRNA but also to diagnosis of mRNA.

First and second DNA primer sets comprising primers having base sequences of R1–XY and R2–ZW (wherein X, Y, Z and W are any one of A, T, G and C), respectively, may also be employed instead of the first and second DNA primer sets (R1–X, R2–X, wherein X is A, T, G or C). Such first and second primer sets comprises 16 combinations of bases X and Y and 16 combinations of bases Z and WY and thus there are 16×16=256 combinations of the primers, as explained in Example 1. Accordingly, a solution containing the DNA fragments digested with two restriction enzymes and added with polyA tail 42 at the 3'-end thereof is dispensed into 256 fractions followed by the treatment as described above. Electrophoresis of the fractions in 256 different lanes gives quite the same results as shown in FIG. 2. Where different four kinds of labels are employed as fluorescent labels of the 5'-end of each primer of the first DNA primer set, complementary strand synthesis using the primers having different four fluorescent labels from the first DNA primer set can be carried out in the same tube. The products obtained by complementary strand synthesis performed in 64 tubes can be electrophoresed in a single-stranded form in 64 lanes corresponding to the tubes.

As explained above, sample DNA is digested with a plurality of restriction enzymes and complementary strand synthesis is performed using a plurality of DNA primer sets thereby to obtain and isolate the DNA fragments having a definite base sequence at the 5'-end thereof contiguous to the base sequence complementary all of the recognition sequences of the restriction enzymes or complementary to a part of the 3'-end of the recognition sequences. Thus, a plurality of spectra of the DNA fragments from sample DNA are obtained. The resulting spectra of the DNA fragments can be utilized not only for a more detailed analysis of sample DNA but also diagnosis and the like.

EXAMPLE 3

Example 3 relates to an embodiment of the present invention which is applicable to analysis of mRNAs extracted from cells using polyA tail.

Figure 5:
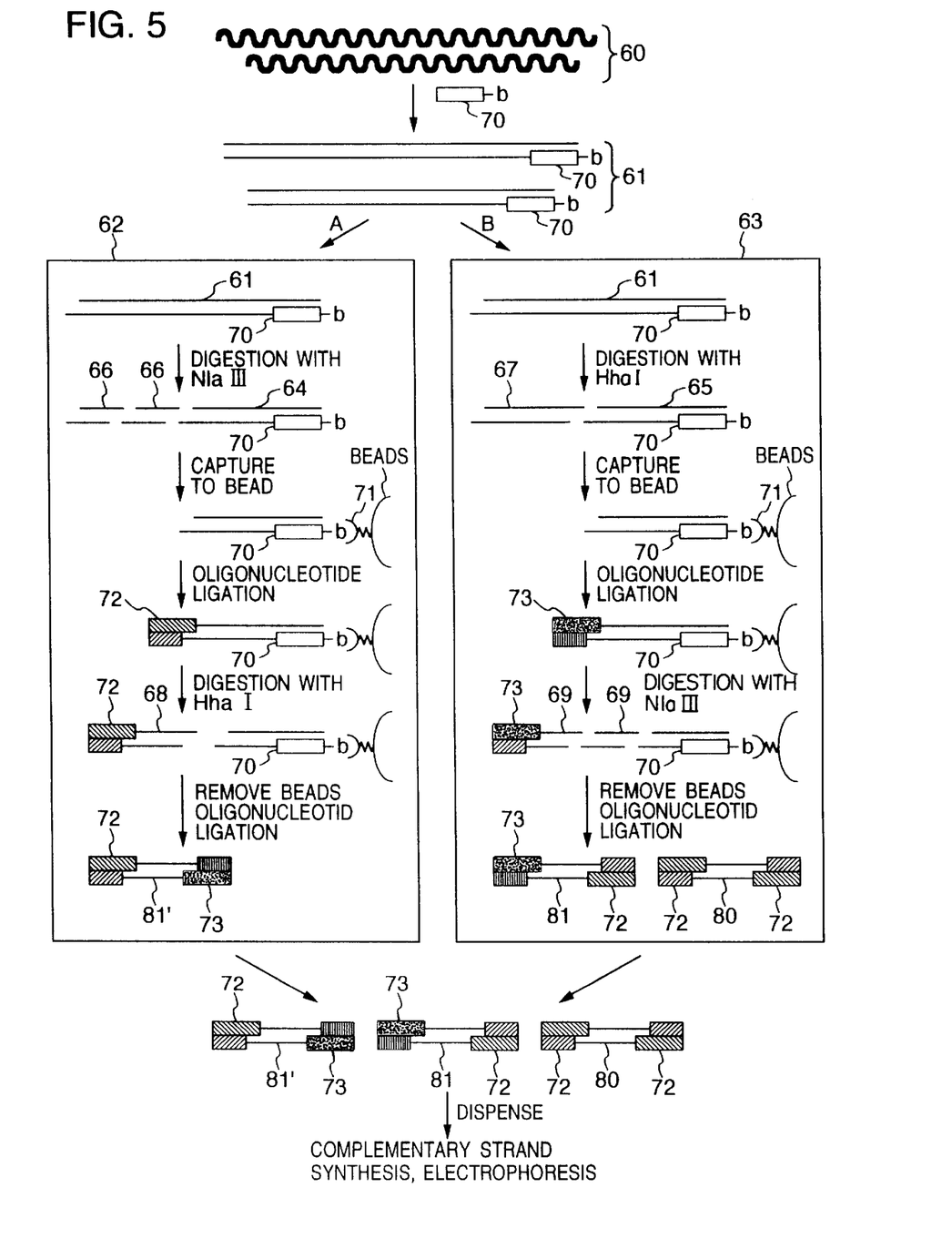
FIG. 5 is a drawing for explaining the procedures in Example 3 of the present invention, in which a mixture of double-stranded cDNAs prepared from mRNA is digested with two different restriction enzymes followed by complementary strand synthesis to obtain DNA fragments.

FIG. 5 is a drawing for explaining the procedures in Example 3 of the present invention, in which a mixture of double-stranded cDNAs prepared from mRNA is digested with two different restriction enzymes followed by complementary strand synthesis to obtain DNA fragments having a definite base sequence at the 5'-end thereof contiguous to the recognition sequences by restriction enzymes. According to the prior art (Sambrook et al., Molecular Cloning, A Laboratory Manual, 2nd edition, 7.1–7.36 (1987), Cold Spring Harbor Laboratory press), cell membrane is lysed by treating culture cells with lysis buffer containing 1% SDS followed by treatment with proteinase K. By centrifugation nucleic acids components in the cells are extracted. Using an oligo dT column, mRNA 60 (mixture) containing polyA tail is obtained from the nucleic acids components. Then double-stranded cDNA 61 (mixture) is prepared from mRNA 60 using reverse transcriptase, biotinylated oligo dT primer 70 and DNA polymerase. The thus obtained double-stranded cDNA 61 (mixture) is dispensed into fraction A (62) and fraction B (63). The double-stranded cDNA in fraction A (62) is digested with restriction enzyme NlaIII and the double-stranded cDNA in fraction B is digested with restriction enzyme HhaI.

Among the digested fragments, the digested fragment 64 of biotinylated (b) double-stranded cDNA digested with NlaIII and the digested fragment 65 of biotinylated (b) double-stranded cDNA digested with HhaI are captured to avidin 71 bound to beads to remove the digested fragment 66 of non-biotinylated (b) double-stranded cDNA digested with NlaIII and the digested fragment 67 of non-biotinylated (b) double-stranded cDNA digested with HhaI. Double-stranded oligonucleotides 72 (which hybridize to the NlaIII digestion site) and 73 (which hybridize to the HhaI digestion site) having known base sequences which hybridize to the digestion site with each restriction enzyme are ligated to the double-stranded cDNA at the ends thereof in each fraction.

The double-stranded cDNA in fraction A (62) is digested with restriction enzyme HhaI and the double-stranded cDNA in fraction B (63) is digested with restriction enzyme NlaIII. Beads are removed from each fraction to remove from each fraction the double-stranded cDNA captured to beads through binding between avidin 71 to beads and biotin b. Thus, the fragment 68 digested with HhaI which is not captured to beads and the fragment 69 digested with NlaIII which is not captured to beads are left in each fraction. There are obtained double-stranded cDNA fragments 81 and 81' ligated to the double-stranded oligonucleotides 72 and 73 having known base sequences which hybridize to the digestion site by each restriction enzyme.

In double-stranded cDNA in which the recognition sites by restriction enzymes are located in the order of the 3'-end, NlaIII and HhaI, double-stranded cDNA fragment 81 digested at two restriction enzyme sites is obtained in fraction B. Conversely in double-stranded cDNA in which the recognition sites by restriction enzymes are located in the order of HhaI and NlaIII, double-stranded cDNA fragment 81' digested at two restriction enzyme sites is obtained in fraction A. Double-stranded cDNA fragment 80, both ends of which are digested with the same restriction enzyme may be formed sometimes but such a fragment can be discriminated by the following complementary strand synthesis.

Subsequently, the double-stranded cDNA fragments obtained from fractions A and B are mixed and the resulting mixture is subjected to complementary strand synthesis using a first DNA primer set (having a base sequence portion complementary to the recognition sequence by restriction enzyme NlaIII) and a second DNA primer set (having a base sequence portion complementary to the recognition sequence by restriction enzyme HhaI), in a manner similar to Example 1 or 2. The products obtained by the complementary strand synthesis are electrophoresed in different lanes corresponding to the combinations of the primers from the first and second DNA primer sets. The thus obtained electropherograms are used for analysis of DNA. Where the DNA primer set comprising 16 primers explained in Example 1 is used, the resulting electropherograms become 16×16=256 kinds. Where the DNA primer set comprising 4 primers explained in Example 2 is used, the resulting electropherograms become 4×4=16 kinds. Where the first DNA primer set comprises 4 primers using one base as a selective sequence and the second DNA primer set comprises 16 primers using two bases as a selective sequence, the first and second DNA primer sets have 4×16=64 combinations of the primers. Thus the resulting electropherograms of the DNA fragments become 4×16=64 kinds.

As explained above, DNA diagnosis technique using conventional DNA primers can only inspect, at most, several to ten DNA fragments by a single test but is unsuitable for inspection of several hundred to several thousand cDNAs or DNA fragments. Furthermore, such a technique was not available for inspection of a long DNA unknown to find abnormality where. According to the present invention, using a plurality of DNA primer sets having ligated oligonucleotide at the 3'-end of the DNA fragment and 1 to 4 base sequences (selective sequences) which can hybridize to all or part of the base sequences recognized by restriction enzymes to discriminate if hybridization to a desired DNA fragment occurs at the 3'-end, DNA fragments can be selectively discriminated, and complementary strand synthesis is performed for amplification. The DNA fragments are electrophoresed in different lanes corresponding to the combinations of the primers from a plurality of DNA primer sets. Fingerprint can be obtained from migration patterns representing the lengths of the complementary strands synthesized. Therefore, the present invention provides a new method for fingerprinting and DNA analysis which can overcome the problems in the prior art. As stated above, by using a plurality of DNA primer sets, sample DNA can be classified in a simple manner, which enables to analyze a sample containing a large number of DNA fragments.

The restriction enzyme used in the present invention provides any one of 3'-overhang end, 3'-blunt end and 5'-overhang end. It is convenient to add polyN tail (any one of polyA tail, polyC tail, polyG tail and polyT tail) to the oligonucleotide introduced at the end of the DNA fragment which gives the 3'-blunt end by restriction enzyme.

In the Examples explained above, where electropherograms (fingerprint patterns) are extremely complicated, each DNA primer in the DNA primer sets used in the foregoing Examples is previously biotinylated and only the finally synthesized complementary strands are captured. The captured DNA fragments are regarded as a new sample. The kind of restriction enzymes used in the Examples are modified and the procedures in the Examples are again performed. The thus obtained electropherograms (fingerprinting patterns) can be more readily discriminated so that a sample can be analyzed more accurately. That is, according to the present invention, information on lengths from a large number of DNA fragments are not utilized as fingerprints as originally given; instead, sample DNA is digested with a plurality of restriction enzymes, the resulting DNA fragments are classified into groups in terms of the terminal base sequence adjacent to the site digested with the restriction enzyme. The fragment length is measured in every group and used as fingerprinting. Therefore, the present invention is advantageous in that the same fragment lengths do not overlap with each other to provide a high resolution of the DNA fragments and resolution can be regulated by modifying the combination of restriction enzymes.

The present invention is summarized below. The method of the present invention for analysis of nucleic acid comprises:

(1) a step of digesting a sample DNA with a plurality of restriction enzymes to obtain DNA fragments;

(2) a step of ligating an oligonucleotide containing deoxynucleotide or an analogue thereto to the DNA fragments at the both ends thereof;

(3) a step of performing a complementary strand synthesis reaction of the region of the DNA fragments between the base sequences recognized by different restriction enzymes, using labeled primers from at least two DNA primer sets having the base sequence of the ligated oligonucleotide, the base sequence contiguous to the base sequence of the ligated oligonucleotide and complementary to a part or all of the base sequences recognized by the restriction enzymes and a selective sequence of 1 to 3 bases at the 3'-end thereof (4 kinds of labeled DNA primers when the selective base sequence is one base, 16 kinds when it is two bases and 64 kinds when it is three bases); and, (4) a step of electrophoresing the products obtained by the complementary strand synthesis reaction and detecting the DNA fragments.

The method of the present invention further includes the following features.

(a) The nucleic acid sample is RNA and RNA is converted into DNA strand using reverse transcriptase.

(b) The 3'-terminal base sequences of 1 to 3 bases in the DNA primers cover combinations of substantially all bases and the DNA primers are labeled with any one of a radioisotope, biotin and fluorophore.

(c) The DNA fragment of the region between the base sequences recognized by two restriction enzymes is produced and labeled by complementary strand synthesis using two primers at the same time comprising a plurality of DNA primer sets having all possible base sequences of 1 to 3 bases at the 3'-ends thereof.

(d) The restriction enzymes can provide any one of 3'-overhang end, 3'-blunt end and 5'-overhang end.

The DNA primers in the DNA primer sets used in the method for analysis of nucleic acid according to the present invention have a structure represented by:

wherein $N_1N_2 \ldots N_n$ ($5 \leq n \leq 27$) represents a base sequence substantially complementary to the oligonucleotide ligated with the end of the DNA fragment; $X_1X_2 \ldots X_m$ ($1 \leq m \leq 6$) represents a base sequence complementary to a part or all of the base sequence recognized by restriction enzyme; $Z_1Z_2 \ldots Z_h$ ($0 \leq h \leq 3$) represents a nucleotide analog capable of hybridizing to a plurality of nucleotides; $Y_1Y_2 \ldots Y_k$ ($1 \leq k \leq 4$) represents combinations ($4^k$) of A, C, G and T; and any one of the nucleotides constructing $N_1N_2 \ldots N_n$ is labeled.

The application is based on Japanese Patent Application No. 08-093828 filed in Japan on Apr. 16, 1996, the content of which is incorporated hereinto by reference.

What is claimed is:

1. A method for analysis of a nucleic acid which comprises:

(1) digesting a double-stranded DNA sample with a first restriction enzyme and a second restriction enzyme to obtain double-stranded DNA fragments;

(2) discriminating a difference in base sequences of 1 to 4 bases adjacent to restriction enzyme recognition sites of the double-stranded DNA fragments with first labeled DNA primers and second labeled DNA primers, said first labeled DNA primers and second labeled DNA primers each having a 3'- and a 5'-end; and extending said first labeled DNA primers and said second labeled DNA primers, by a complementary strand extension synthesis reaction, to classify the double-stranded DNA fragments into 16 to 65536 groups, wherein said first labeled DNA primers have all possible combinations of 1 to 4 bases selected from A, C, G and T at the 3'-end thereof, and said second labeled DNA primers have all possible combinations of 1 to 4 bases selected from A, C, G and T at the 3'-end thereof;

(3) measuring the lengths of the products produced during said complementary strand extension synthesis reaction, by electrophoresis; and, (4) classifying measured lengths of the products produced during said complementary strand extension synthesis reaction into 16 to 65536 groups by the differences in base sequences of 1 to 4 bases adjacent to the restriction enzyme recognition sites of the double-stranded DNA fragments to obtain fingerprinting patterns of said DNA fragments, wherein the restriction enzyme recognition sites are recognized by said first and second restriction enzymes, respectively.

2. A method for analysis of nucleic acid which comprises:
(1) digesting a double-stranded DNA sample with a first restriction enzyme to obtain double-stranded DNA fragments;
(2) ligating a first oligonucleotide having known base sequence to both ends of each of said double-stranded DNA fragments;
(3) digesting products obtained in step (2) with a second restriction enzyme to obtain double-stranded DNA fragments;
(4) ligating a second oligonucleotide having known base sequence to one end or both ends of each of said double-stranded DNA fragments obtained in step (3), to obtain ligated double-stranded DNA fragments;
(5) capturing one end of each of the ligated double-stranded DNA fragments each having, at said one end, said first oligonucleotide, and having at another end, said second oligonucleotide;
(6) converting the ligated double-stranded DNA fragments captured in step (5) into single-stranded DNA fragments and then dispensing a solution containing the single-stranded DNA fragments into a plurality of tubes;
(7) adding a first DNA primer selected from a first labeled DNA primer set and a second primer selected from a second DNA primer set to said respective tubes for each of combinations of said first DNA primer and said second DNA primer, and extending said first DNA primer and said second DNA primer, by a complementary strand extension synthesis reaction in said respective tubes,
wherein each of the primers of said first labeled DNA primer set has a 3'- and a 5'-end, and has at the 5'-end of each of the primers of said first labeled DNA primer set, a first base sequence complementary to at least a part of the base sequence recognized by said first restriction enzyme and has, at the 3'-end, a first selective base sequence of 1 to 4 bases, said first selective base sequence discriminates a difference in base sequences of 1 to 4 bases adjacent to the 5'-end of the base sequence recognized by said first restriction enzyme in each of the single-stranded DNA fragments, and the primers of said first labeled DNA primer set have all possible combinations of 1 to 4 bases selected from A, C, G and T at the 3'-end thereof,
and wherein each of the primers of said second DNA primer set has a 3'- and a 5'-end, and at the 5'-end, a second base sequence complementary to at least a part of the base sequence recognized by said second restriction enzyme and has, at the 3'-end, a second selective base sequence of 1 to 4 bases, said second selective base sequence discriminates a difference in base sequences of 1 to 4 bases directly connected to the 5'-end of the base sequence recognized by said second restriction enzyme in each of the single-stranded DNA fragments, and the primers of second DNA primer set have, at the 3'-end, all possible combinations of 1 to 4 bases selected from A, C, G and T;
(8) measuring the lengths of the products produced during said complementary strand extension synthesis reaction in said respective tubes in step (7), by electrophoresis; and (9) classifying measured lengths of the products produced during said complementary strand extension synthesis reaction into 16 to 65536 groups by the differences in base sequences of 1 to 4 bases adjacent to the restriction enzyme recognition sites of the ligated double-stranded DNA fragments to obtain fingerprinting patterns of said DNA fragments, wherein the restriction enzyme recognition sites are recognized by said first and second restriction enzymes, respectively.

3. A method according to claim 2, wherein the products obtained by said complementary strand synthesis reaction in the respective tubes in step (7) are subjected to electrophoresis in different lanes, respectively.

4. A method for analysis of nucleic acid which comprises:
(1) digesting a double-stranded DNA sample with a first restriction enzyme and a second restriction enzyme to obtain double-stranded DNA fragments;
(2) ligating a single-stranded oligonucleotide having known base sequence to 3'-ends of each of said double-stranded DNA fragments;
(3) dispensing double-stranded DNA fragments obtained in step (2) into a plurality of tubes and then converting said double-stranded DNA fragments obtained in step (2) into single-stranded DNA fragments in said respective tubes to obtain first single-stranded DNA fragments and second single-stranded DNA fragments;
(4) adding a first DNA primer selected from a first labeled DNA primer set and a second DNA primer selected from a second labeled DNA primer set to said respective tubes for each of combinations of said first DNA primer and said second DNA primer, and extending said first DNA primer and said second DNA primer hybridized with the single-stranded DNA fragment, by a complementary strand extension synthesis reaction in said respective tubes,
wherein each of the primers of said first labeled DNA primer set has a 3'- and a 5'-end, and has at the 5'-end, a first base sequence complementary to at least a part of the base sequence recognized by said first restriction enzyme and has, at the 3'-end, a first selective base sequence of 1 to 4 bases, said first selective base sequence discriminates a difference in base sequences of 1 to 4 bases adjacent to the 5'-end of the base sequence recognized by said first restriction enzyme in each of the first single-stranded DNA fragments, and the primers of said first labeled DNA primer set have, at the 3'-end, all possible combinations of 1 to 4 bases selected from A, C, G and T,
and wherein each of the primers of said second labeled DNA primer set has a 3'- and a 5'-end, and has at the 5'-end, a second base sequence complementary to at least a part of the base sequence recognized by said second restriction enzyme and has, at the 3'-end, a second selective base sequence of 1 to 4 bases, said second selective base sequence discriminates a difference in base sequences of 1 to 4 bases adjacent to the 5'-end of the base sequence recognized by said second restriction enzyme in the second single-stranded DNA fragments, and the primers of said second labeled DNA primer set have, at the 3'-end, all possible combinations of 1 to 4 bases selected from A, C, G and T;
(5) measuring the lengths of products produced during said complementary strand extension synthesis reaction in said respective tubes in step (4), by electrophoresis; and,
(6) classifying measured lengths of the products produced during said complementary strand extension synthesis reaction into 16 to 65536 groups by the differences in base sequences of 1 to 4 bases adjacent to the restriction enzyme recognition sites of the double-stranded DNA fragments obtained in step (2) to obtain fingerprinting patterns of said DNA fragments, wherein the restriction enzyme recognition sites are recognized by said first and second restriction enzymes, respectively.

5. A method according to claim 4, wherein the products obtained in step (4) by said complementary strand synthesis reaction in the respective tubes are subjected to electrophoresis in different lanes.

6. A method according to claim 4, wherein said single-stranded oligonucleotide comprises a poly N tail, wherein N is selected from A, T, G and C.

7. A method according to claim 4, wherein said double-stranded DNA sample is obtained from a RNA sample using a reverse transcriptase.

8. A method according to claim 4, wherein said first labeled DNA primer set comprises 4 primers having, at the 3'-end, all possible combinations of 1 base selected from A, C, G and T, and said second labeled DNA primer set comprises 4 primers having, at the 3'-end, all possible combinations of 1 base selected from A, C, G and T.

9. A method according to claim 4, wherein said first labeled DNA primer set comprises 16 primers having, at the 3'-end, all possible combinations of 2 bases selected from A, C, G and T, and said second labeled DNA primer set comprises 16 primers having, at the 3'-end, all possible combinations of 2 bases selected from A, C, G and T.

10. A method for analysis of nucleic acid which comprises:
  (1) digesting a double-stranded DNA sample with a first restriction enzyme and a second restriction enzyme to obtain double-stranded DNA fragments,
  (2) discriminating a difference in base sequences of 1 to 4 bases adjacent to restriction enzyme recognition sites of the double-stranded DNA fragments with first labeled DNA primers and second DNA primers, and extending said first labeled DNA primers and said second DNA primers, by a complementary strand extension synthesis reaction, to classify the double-stranded DNA fragments into 16 to 65536 groups,
  wherein said first labeled DNA primers have a 3'- and a 5'-end; and have at the 3'-end, all possible combinations of 1 to 4 bases selected from A, C, G and T, and said second DNA primers have, at the 3'-end, all possible combinations of 1 to 4 bases selected from the A, C, G and T;
  (3) measuring the lengths of products produced during said complementary strand extension synthesis reaction, by electrophoresis; and
  (4) classifying measured lengths of the products produced during said complementary strand extension synthesis reaction into 16 to 65536 groups by the differences in base sequences of 1 to 4 bases adjacent to the restriction enzyme recognition sites of the double-stranded DNA fragments to obtain fingerprinting patterns of said DNA fragments, wherein the restriction enzyme recognition sites are recognized by said first and second restriction enzymes.

11. A method for analysis of nucleic acid which comprises:
  (1) digesting a double-stranded DNA sample with a first restriction enzyme and a second restriction enzyme to obtain double-stranded DNA fragments;
  (2) discriminating a difference in base sequences of 1 to 4 bases adjacent to restriction enzyme recognition sites of the double-stranded DNA fragments with first labeled DNA primers and second labeled DNA primers, and extending, by a complementary strand extension synthesis reaction, each of first labeled DNA primers hybridized with each of first single-stranded DNA fragments obtained from the double-stranded DNA fragments and each of second labeled DNA primers hybridized with each of second single-stranded DNA fragments obtained from the double-stranded DNA fragments, to classify the double-stranded DNA fragments into 16 to 65536 groups,
  wherein said first labeled DNA primers have a 3'- and a 5'-end; and have at the 3'-end, all possible combinations of 1 to 4 bases selected from A, C, G and T, and said second labeled DNA primers each have, at the 3'-end, all possible combinations of 1 to 4 bases selected from A, C, G and T;
  (3) measuring the lengths of products produced during said complementary strand extension synthesis reaction, by electrophoresis; and,
  (4) classifying measured lengths of the products produced during said complementary strand extension synthesis reaction into 16 to 65536 groups by the differences in bases sequences of 1 to 4 bases adjacent to the restriction enzyme recognition sites of the double-stranded DNA fragments to obtain fingerprinting patterns of said DNA fragments, wherein the restriction enzyme recognition sites are recognized by said first and second restriction enzymes.

12. A method for analysis of nucleic acid which comprises:
  (1) dispensing double-stranded DNA samples into a first fraction and a second fraction;
  (2) digesting said double-stranded DNA samples of said first fraction with a first restriction enzyme to obtain double-stranded DNA fragments and capturing one end of said double-stranded DNA fragments on a first support;
  (3) ligating a first oligonucleotide having a known base sequence to another end of each of said double-stranded DNA fragments captured on said first support;
  (4) digesting said double-stranded DNA fragments captured and ligated in step (3) with a second restriction enzyme to obtain double-stranded DNA fragments;
  (5) removing said first support from said first fraction to remove the double-stranded DNA fragments captured on said first support;
  (6) ligating a second oligonucleotide having a known base sequence to one end or both ends of each of said double-stranded DNA fragments remaining in the first fraction after steps (4) and (5), to obtain first double-stranded DNA fragments;
  (7) digesting said double-stranded DNA samples of said second fraction with said second restriction enzyme and capturing one end of the double-stranded DNA fragments on a second support;
  (8) ligating said second oligonucleotide to another end of each of said double-stranded DNA fragments captured on said second support;
  (9) digesting said double-stranded DNA fragments captured and ligated in step (8) with said first restriction enzyme to obtain double-stranded DNA fragments;
  (10) removing said second support from said second fraction to remove the double-stranded DNA fragments captured on said second support;

(11) ligating said first oligonucleotide to one end or both ends of said double-stranded DNA fragments remaining in the second fraction after steps (9) and (10), to obtain second double-stranded DNA fragments;

(12) dispensing a mixture of said first double-stranded DNA fragments obtained in step (6) and said second double-stranded DNA fragments obtained in step (11) into a plurality of tubes, and then converting said first and second double-stranded DNA fragments into single-stranded DNA fragments in said respective tubes to obtain first single-stranded DNA fragments and second single-stranded DNA fragments;

(13) adding a first DNA primer selected from a first labeled DNA primer set and a second DNA primer selected from a second labeled DNA primer set to said respective tubes for each of combinations of said first DNA primer and said second DNA primer, and extending said first DNA primer hybridized with the first single-stranded DNA fragment and said second DNA primer hybridized with the second single-stranded DNA fragment, by a complementary strand extension synthesis reaction in said respective tubes, wherein each of primers of said first labeled DNA primer set has a 3'- and a 5'-end, and has at the 5'-end, a first base sequence complementary to at least a part of the base sequence recognized by said first restriction enzyme and has, at the 3'-end, a first selective base sequence of 1 to 4 bases, said first selective base sequence discriminates a difference in base sequences of 1 to 4 bases adjacent to the 5'-end of the base sequence recognized by said first restriction enzyme in each of the first single-stranded DNA fragments, and the primers of said first labeled DNA primer set have, at the 3'-end, all possible combinations of 1 to 4 bases selected from A, C, G and T, and wherein each of the primers of said second labeled DNA primer set has a 3'- and a 5'-end, and has at the 5'-end, a second base sequence complementary to at least a part of the base sequence recognized by said second restriction enzyme and has, at the 3'-end, a second selective base sequence of 1 to 4 bases, said second selective base sequence discriminates a difference in base sequences of 1 to 4 bases adjacent to the 5'-end of the base sequence recognized by said second restriction enzyme in the second single-stranded DNA fragments, and the primers of said second labeled DNA primer set have, at the 3'-end, all possible combinations of 1 to 4 bases selected from A, C, G and T;

(14) measuring the lengths of products produced during said complementary strand extension synthesis reaction, by electrophoresis; and, (15) classifying measured lengths of the products produced during said complementary strand extension synthesis reaction into 16 to 65536 groups by the differences in base sequences of 1 to 4 bases adjacent to the restriction enzyme recognition sites of the first double-stranded DNA fragments and the second double-stranded DNA fragments to obtain fingerprinting patterns of said DNA fragments, wherein the restriction enzyme recognition sites are recognized by said first and second restriction enzymes.

13. A method according to claim 12, wherein said double-stranded DNA samples are obtained from a RNA sample using a reverse transcriptase.

14. A method according to claim 12, wherein said first labeled DNA primer set comprises 4 primers having, at the 3'-end, all possible combinations of 1 base selected from A, C, G and T, and said second labeled DNA primer set comprises 4 primers having, at the 3'-end, all possible combinations of 1 base selected from A, C, G and T.

15. A method according to claim 12, wherein said first labeled DNA primer set comprises 16 primers having, at the 3'-end, all possible combinations of 2 bases selected from A, C, G and T, and said second labeled DNA primer set comprises 16 primers having, at the 3'-end, all possible combinations of 2 bases selected from A, C, G and T.

16. A method according to claim 12, wherein said first labeled DNA primer set comprises 4 primers having, at the 3'-end, all possible combinations of 1 base selected from A, C, G and T, and said second labeled DNA primer set comprises 16 primers having, at the 3'-end, all possible combinations of 2 bases selected from A, C, G and T.

17. A method for analysis of nucleic acid which comprises:

(1) digesting a double-stranded DNA sample with a plurality of restriction enzymes to obtain double-stranded DNA fragments;

(2) ligating a single-stranded oligonucleotide having known base sequence to 3'-ends of each of said double-stranded DNA fragments;

(3) dispensing double-stranded DNA fragments obtained in step (2) into a plurality of tubes and then converting said double-stranded DNA fragments obtained in step (2) into single-stranded DNA fragments in said respective tubes to obtain first single-stranded DNA fragments and second single-stranded DNA fragments;

(4) adding a first DNA primer selected from a first DNA primer set which is one set in two sets selected from labeled DNA primer sets and a second DNA primer selected from a second DNA primer set which is another set of the two sets selected from said labeled DNA primer sets, to said respective tubes for each of combinations of the first DNA primer and the second DNA primer, and extending said first DNA primer hybridized with the first single-stranded DNA fragment and said second DNA primer hybridized with the second single-stranded DNA fragment, by a complementary strand extension synthesis reaction in said respective tubes, wherein labeled DNA primer sets correspond to said restriction enzymes, respectively, and the number of labeled DNA primer sets is equal to the number of species of said restriction enzymes, and wherein each of the primers of said first DNA primer set has a 3'- and a 5'-end, and has at the 5'-end, a first base sequence complementary to at least a part of the base sequence recognized by a first restriction enzyme and has, at the 3'-end, a first selective base sequence of 1 to 4 bases, said first selective base sequence discriminates a difference in base sequences of 1 to 4 bases adjacent to the 5'-end of the base sequence recognized by said first restriction enzyme in each of the first single-stranded DNA fragments, and the primers of said first DNA primer set have, at the 3'-end, all possible combinations of 1 to 4 bases selected from A, C, G and T, and wherein each of the primers of said second DNA primer set has a 3'- and a 5'-end, and has at the 5'-end, a second base sequence complementary to at least a part of the base sequence recognized by a second restriction enzyme and has, at the 3'-end, a second selective base sequence of 1 to 4 bases, said second selective base sequence discriminates a difference in base sequences of 1 to 4 bases adjacent to the 5'-end of the base sequence recognized by said second restriction enzyme in each of the second single-stranded DNA fragments, and the primers of said second DNA primer set have, at the 3'-end, all possible combinations of 1 to 4 bases selected from A, C, G and T, (5) measuring the lengths of products produced during said complementary strand extension synthesis reaction in step (4) for all possible combinations of two sets in said labeled DNA primer sets, by electrophoresis; and (6) classifying measured lengths of the products produced during said complementary strand extension synthesis reaction in step (5) into 16 to 65536 groups by the differences in base sequences of 1 to 4 bases adjacent to the restriction enzyme recognition sites of the double-stranded DNA fragments obtained in step (2) to obtain fingerprinting patterns of said DNA fragments, wherein the restriction enzyme recognition sites are recognized by two different restriction enzymes.

18. A method according to claim 17, wherein said double-stranded DNA sample is digested with three restriction enzymes in step (1).

19. A method according to claim 17, wherein said double-stranded DNA samples are obtained from a RNA sample using a reverse transcriptase.

20. A method according to claim 17, wherein said double-stranded DNA sample is digested with three restriction enzymes in step (1), said three restriction enzymes comprises a first restriction enzyme, a second restriction enzyme and a third restriction enzyme, said labeled DNA primer sets comprises a first labeled DNA primer set, a second labeled DNA primer set and a third labeled DNA primer set comprising, respectively, 4 primers having, at the 3'-end, all possible combinations of 1 base selected from A, C, G and T.

21. Method according to claim 17, wherein said fingerprinting patterns of said DNA fragments are compared with DNA obtained from a patient sample and are used in the diagnosis of disease.

* * * * *